(12) United States Patent
Kurisawa et al.

(10) Patent No.: US 9,687,464 B2
(45) Date of Patent: Jun. 27, 2017

(54) ANTI-CANCER AGENT DELIVERY VEHICLES CAPABLE OF IMPROVED LOADING

(75) Inventors: Motoichi Kurisawa, Singapore (SG); Kun Liang, Singapore (SG); Susi Tan, Singapore (SG); Joo Eun Chung, Singapore (SG); Jackie Y. Ying, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/634,036

(22) PCT Filed: Mar. 11, 2011

(86) PCT No.: PCT/SG2011/000100
§ 371 (c)(1),
(2), (4) Date: Dec. 21, 2012

(87) PCT Pub. No.: WO2011/112156
PCT Pub. Date: Sep. 15, 2011

(65) Prior Publication Data
US 2013/0004488 A1    Jan. 3, 2013

Related U.S. Application Data

(60) Provisional application No. 61/312,885, filed on Mar. 11, 2010.

(51) Int. Cl.
| | |
|---|---|
| *A61K 31/33* | (2006.01) |
| *A61K 31/282* | (2006.01) |
| *A61K 9/00* | (2006.01) |
| *A61K 9/107* | (2006.01) |
| *A61K 31/337* | (2006.01) |
| *A61K 31/353* | (2006.01) |
| *A61K 31/704* | (2006.01) |
| *A61K 31/7088* | (2006.01) |
| *A61K 45/06* | (2006.01) |
| *A61K 47/48* | (2006.01) |

(52) U.S. Cl.
CPC .......... *A61K 31/282* (2013.01); *A61K 9/0019* (2013.01); *A61K 9/1075* (2013.01); *A61K 31/337* (2013.01); *A61K 31/353* (2013.01); *A61K 31/704* (2013.01); *A61K 31/7088* (2013.01); *A61K 45/06* (2013.01); *A61K 47/48215* (2013.01)

(58) Field of Classification Search
CPC .... A61K 31/82; A61K 31/337; A61K 31/353; A61K 31/704; A61K 47/48215
See application file for complete search history.

(56) References Cited

U.S. PATENT DOCUMENTS

| | | | |
|---|---|---|---|
| 7,858,080 B2 * | 12/2010 | Chung et al. | 424/78.3 |
| 9,248,200 B2 | 2/2016 | Ying et al. | |
| 2008/0102052 A1 * | 5/2008 | Chung et al. | 424/78.3 |
| 2011/0044992 A1 * | 2/2011 | Ying et al. | 424/143.1 |

FOREIGN PATENT DOCUMENTS

| | | | | |
|---|---|---|---|---|
| WO | WO 03/044026 | * | 5/2003 | C07F 7/18 |
| WO | WO-2006/124000 A1 | | 11/2006 | |
| WO | WO-2009/054813 A1 | | 4/2009 | |
| WO | WO-2010/138082 A1 | | 12/2010 | |
| WO | WO-2011/019323 A1 | | 2/2011 | |

OTHER PUBLICATIONS

Dangerfield EM, Plunkett CH, Win-Mason AL, Stocker BL, Timmer MS. Protecting-group-free synthesis of amines: synthesis of primary amines from aldehydes via reductive amination. J Org Chem. Aug. 20, 2010;75(16):5470-7.*
Handbook of Pharmceutical Biotechnology (pp. 444-447, 2007).*
Akama et al (J Med Chem 39:3461-3469, 1996).*
International Search Report and Written Opinion for PCT/SG2011/000100, dated May 31, 2011, 12 pages.
Ihara, N. et al., Amplification of Inhibitory Activity of Catechin against Disease-Related Enzymes by Conjugation on Poly(e-lysine), Biomacromolecules, 5: 1633-1636 (2004).

* cited by examiner

*Primary Examiner* — Craig Ricci
(74) *Attorney, Agent, or Firm* — Choate, Hall & Stewart LLP (57) ABSTRACT

There is provided a conjugate of a delivery agent containing a chemical moiety and at least one flavonoid. The flavonoid exists in a monomeric form or dimeric form before conjugation and remains in the monomeric form or dimeric form after conjugation. Preferably, the conjugate comprises two flavonoids. The delivery agent is conjugated at the C6 and/or the C8 position of the A ring of the flavonoid. An anti-cancer agent delivery vehicle comprising an anti-cancer agent and the conjugate is also provided.

12 Claims, 8 Drawing Sheets

ANTI-CANCER AGENT DELIVERY VEHICLES CAPABLE OF IMPROVED LOADING

CROSS-REFERENCE TO RELATED APPLICATION

This application claims the benefit of U.S. Provisional Patent Application No. 61/312,885 filed on 11 Mar. 2010, the entire contents of which are incorporated herein by reference.

FIELD OF INVENTION

The invention relates generally to anti-cancer agent delivery vehicles capable of improved loading.

BACKGROUND TO THE INVENTION

The following discussion of the background to the invention is intended to facilitate an understanding of the present invention. However, it should be appreciated that the discussion is not an acknowledgment or admission that any of the material referred to was published, known or part of the common general knowledge in any jurisdiction as at the priority date of the application.

In the design and development of novel drug delivery systems, polymeric micelles, for instance, have attracted considerable attention due to their potential for use as drug delivery vehicles for anti-cancer drugs to target tumor tissues. Briefly, a micelle is an aggregate of amphiphilic or surfactant molecules dispersed in a liquid colloid. Each of the amphiphilic/surfactant molecules has a hydrophilic "head" end and a hydrophobic "tail" end. The tails of the micelle may include hydrocarbon groups, and the heads of the micelle may include charged (anionic or cationic) groups or polar groups. In a polar solvent such as an aqueous liquid, an aggregate of the micelle molecules typically form a normal micelle with the hydrophilic head ends extending outward and in contact with the surrounding solvent, sequestering the hydrophobic tail ends in the micelle centre, thereby forming the hydrophobic core. The polymeric micelles are generally formed from the self-assembly of amphiphilic block copolymers in an aqueous environment. It is known that polymeric micelles allow for enhanced accumulation of anti-cancer drug (i.e. enhanced drug loading) at tumor sites due to the enhanced permeability and retention (EPR) effect resulting from the leakiness of tumor vasculature (H. Maeda, *Adv. Enzyme Regul.* 2001, 41, 189-207). In addition, the outer hydrophilic shell of the micelles prevents the adhesion of proteins and reduces the uptake of micelles by the reticuloendothelial system (RES), thereby prolonging the blood circulation of micelles in the body (A. Lavasanifar et al, *Adv. Drug. Deliv. Rev.* 2002, 54, 169-190).

Over the past two decades, many groups have developed polymeric micelles comprising of amphiphilic block copolymers of poly(ethylene glycol) ("PEG" for short) and hydrophobic polymers such as poly($\alpha$/$\beta$-aspartic acid) block copolymer ("PEG-P(Asp)" for short), poly(L-glutamate) block copolymer ("PEG-P(Glu)" for short) and poly(L-lysine)-succinate (N. Nishiyama et al, *Langmuir,* 1999, 15, 377-383, N. Nishiya et al, *Bioconjugate Chem.* 2003, 14, 449-457 and A. A. Bogdanov et al, *Bioconjugate Chem.* 1996, 7, 144-149). Different methods have been developed to encapsulate anti-cancer drugs, such as doxorubicin, cisplatin and proteins, within the micellar core (H. M. Aliabadi, *Polymeric Micelles for Drug Delivery,* 2006, 3, 139-162). Furthermore, in-vivo studies have demonstrated that these micelles have higher anti-tumor efficacy because the drugs encapsulated in the polymeric micelles accumulate in tumor tissues more effectively than the free drugs themselves (N. Nishiyama, *Cancer Research,* 2003, 63, 8977-8983). However, one problem prevalent in these polymeric micelle systems is that the drug loading in such micelles is often very low. In other words, the drug only constitutes a small proportion of the polymeric micelle by weight.

Although the above discussion focuses on polymeric micelles, other drug delivery systems such as matrix delivery systems and drug targeting systems also face similar problem of low drug loading for effective drug delivery.

It is therefore desirable to provide for anti-cancer agent delivery vehicles that overcomes, or at least alleviates, one of the above mentioned problems.

SUMMARY OF THE INVENTION

Throughout this document, unless otherwise indicated to the contrary, the terms "comprising", "consisting of", and the like, are to be construed as non-exhaustive, or in other words, as meaning "including, but not limited to".

In accordance with a first aspect of the invention, there is provided a conjugate of a delivery agent containing a chemical moiety and at least one flavonoid, wherein the flavonoid exists in a monomeric form or dimeric form before conjugation and remains in the monomeric form or dimeric form after conjugation.

Advantageously, the conjugate comprises two or more flavonoids, and each flavonoid does not undergo association with the other flavonoid. In other words, the flavonoids are chemically inert to each other and do not form oligomers during conjugation. The flavonoids may be identical or different.

Preferably, the flavonoid is a catechin-based flavonoid. More preferably, the flavonoid is (−)-epicatechin, (−)-epigallocatechin, (+)-catechin, (−)-epicatechin gallate, or (−)-epigallocatechin gallate. More preferably, the flavonoid is (−)-epigallocatechin gallate. The flavonoid may contain carboxyl-terminated group, amine-terminated group, succinimide-terminated group, or any other group suitable for conjugating with the chemical moiety.

Preferably, the chemical moiety is a polymer. The chemical moiety may be one selected from the group consisting of a polymer having a free aldehyde group or a functional group capable of being converted to an aldehyde group, a polymer having a free carboxyl group or a functional group capable of being converted to a carboxyl group, a polymer having a free amine group or a functional group capable of being converted to an amine group, a polymer having a free succinimide group or a functional group capable of being converted to a succinimide group, and a mixture thereof. More preferably, the polymer is an aldehyde-terminated poly(ethylene glycol), aldehyde-derivatized hyaluronic acid, hyaluronic acid aminoacetylaldehyde diethylacetal conjugate, aldehyde-derivatized hyaluronic acid-tyramine, hyaluronic acid aminoacetylaldehyde diethylacetal conjugate-tyramine, cyclotriphosphazene core phenoxymethyl (methylhydrazono) dendrimer, thiophosphoryl core phenoxymethyl(methylhydrazono) dendrimer, carboxyl-terminated poly(ethylene glycol), amine-terminated poly (ethylene glycol), or succinimide-terminated poly(ethylene glycol). More preferably, the polymer is aldehyde-terminated poly(ethylene glycol).

Preferably, the delivery agent is conjugated at the C6 and/or the C8 position of the A ring of the flavonoid. While the C6 and C8 positions are most preferred, it will be apparent to a person skilled in the art that other conjugation positions of the flavonoid (e.g. at other rings) are also possible.

In accordance with a second aspect of the invention, there is provided a delivery vehicle comprising the conjugate of the first aspect of the invention.

In accordance with a third aspect of the invention, there is provided an anti-cancer agent delivery vehicle comprising an anti-cancer agent and a conjugate of the first aspect of the invention.

In one embodiment, the anti-cancer agent may be a protein, a nucleic acid, a small molecule, a drug, a peptide, an antibody, a hormone, an enzyme, a growth factor, a cytokine, single stranded DNA, double stranded DNA, single stranded RNA, double stranded RNA, a short hairpin RNA, an siRNA, an antibiotic, a chemotherapeutic agent or an angiogenesis inhibitor.

In another embodiment, the anti-cancer agent may be herceptin (trastuzumab) or TNP470, doxorubicin, cisplatin, paclitaxel, daunorubicin, or a mixture thereof.

In accordance with a fourth aspect of the invention, there is provided a pharmaceutical composition comprising the anti-cancer delivery vehicle of the third aspect of the invention.

Advantageously, the pharmaceutical further comprises a pharmaceutical acceptable carrier.

In accordance with a fifth aspect of the invention, there is provided a use of the anti-cancer agent delivery vehicle of the third aspect of the invention for delivering the anti-cancer agent to a cell in for example a subject.

The subject may be a vertebrate preferably a mammal. In one embodiment, the subject is a human.

In another embodiment, the anti-cancer agent delivery vehicle is used to formulate for injection, surgical implantation or topical administration.

In accordance with a sixth aspect of the invention, there is provided a method of conjugating a delivery agent containing a chemical moiety to at least one flavonoid, comprising reacting the delivery agent with the flavonoid, wherein the flavonoid exists in a monomeric form or dimeric form before conjugation and remains in the monomeric form or dimeric form after conjugation.

In accordance with a seventh aspect of the invention, there is provided a method of delivering an anti-cancer agent to a cell.

In one embodiment, the cell is in-vitro.

In another embodiment, the cell is in-vivo and the method comprises administering the anti-cancer agent delivery vehicle to a subject in need of anti-cancer treatment.

The subject may be a vertebrate preferably a mammal. In one embodiment, the subject is a human.

Preferably, the administering of the anti-cancer agent delivery vehicle comprises injecting, surgically implanting or topically applying.

BRIEF DESCRIPTION OF THE DRAWINGS

In the figures, which illustrate, by way of example only, embodiments of the present invention in which:

FIGS. 8 E & F show flow cytometric analysis of cells 48 hours after siRNA transfection. 1000 to 1200 cell events were counted. (E) PEG-EGCG+control siRNA; (F) PEG-EGCG+GFP-22 siRNA.

DETAILED DESCRIPTION

The present invention relates generally to anti-cancer agent delivery vehicles capable of improved drug loading.

The present inventors have in previous attempts developed anti-cancer agent delivery vehicles and methods of the delivery. In WO 2006/124000, conjugates of a delivery agent containing a free aldehyde and a flavonoid where the delivery agent is conjugated at the C6 and/or the C8 position of the A ring of the flavonoid have been provided. In WO 2009/054813, delivery vehicles comprising an anti-cancer agent and a conjugate of a delivery agent containing a free aldehyde and a flavonoid, where the delivery agent is conjugated at the C6 and/or the C8 position of the A ring of the flavonoid have been provided. The contents of both WO 2006/124000 and WO 2009/054813 are herein incorporated by way of reference.

Surprisingly, the inventors have found that the combination of a delivery vehicle containing a chemical moiety and at least one flavonoid, and a bioactive anti-cancer agent has a synergistic anti-cancer effect, greater than the combined effects of each of the delivery vehicle and bioactive anti-cancer agent when used alone. Thus, such delivery vehicles loaded with an anti-cancer agent provide an effective way of delivering anti-cancer agents to a cell, taking advantage of the synergistic effect between the anti-cancer activity of the flavonoid portion of the delivery vehicle and the anti-cancer effect of the anti-cancer agent. It is believed that the synergistic effect and therefore a higher anti-cancer agent loading is due to the flavonoid remaining in its original monomeric form or dimeric form after conjugation with the chemical moiety.

In accordance with one aspect of the invention, there is provided a conjugate of a delivery agent containing a chemical moiety and at least one flavonoid, wherein the flavonoid exists in a monomeric form or dimeric form before conjugation and remains in the monomeric form or dimeric form after conjugation to allow for hydrophobic interactions and/or Π-Π stacking interactions between the flavonoid and other chemical entities such as anti-cancer drugs allowing greater drug loading to the monomeric or dimeric conjugate formed.

Advantageously, the conjugate comprises two or more flavonoids, and each flavonoid does not undergo association with the other flavonoid/s. In other words, the flavonoids are chemically inert to one another and do not form oligomers during conjugation. The flavonoids may be identical or different from one another.

The flavonoid may be any flavonoid from the general class of molecules derived from a core phenylbenzyl pyrone structure, and includes flavones, isoflavones, flavonols, flavanones, flavan-3-ols, catechins, anthocyanidins and chalcones. In a particular embodiment, the flavonoid is a catechin or a catechin-based flavonoid. A catechin, or a catechin-based flavonoid is any flavonoid that belongs to the class generally known as catechins (or flavan-3-ol derivatives), and includes catechin and catechin derivatives, including epicatechin, epigallocatechin, catechin, epicatechin gallate and epigallocatechin gallate, and including all possible stereoisomers of catechins or catechin-based flavonoids.

In particular embodiments, the catechin-based flavonoid is (−)-epicatechin, (−)-epigallocatechin, (+)-catechin, (−)-epicatechin gallate, or (−)-epigallocatechin gallate. (−)-epigallocatechin gallate (EGCG) is thought to have the highest activity among the catechin-based flavonoids, possibly due to the trihydroxy B ring and gallate ester moiety at the C3 position of this flavonoid. In addition, EGCG is particularly chosen to form the conjugate because of its high activity and by conjugation with, say, PEG (to be discussed in subsequent paragraphs), the resultant PEG-EGCG conjugate forms a stable composition that is metabolised or degraded more slowly, and which thus may have a longer half-life in the body. Furthermore, the EGCG moiety is capable of forming interactions, such as hydrophobic interaction, π-π stacking interaction or other physical or chemical bond, with the drug molecule to thereby encapsulate or confine the drug molecule within the inner core of the delivery vehicle.

In certain embodiments, the flavonoid may be EGCG containing carboxyl-terminated group, amine-terminated group, succinimide-terminated group, or any other group suitable for conjugating with the chemical moiety.

Preferably, the delivery agent contains a chemical moiety selected from the group consisting of a polymer having a free aldehyde group or a functional group capable of being converted to an aldehyde group, a polymer having a free carboxyl group or a functional group capable of being converted to a carboxyl group, a polymer having a free amine group or a functional group capable of being converted to an amine group, a polymer having a free succinimide group or a functional group capable of being converted to a succinimide group, and a mixture thereof. In certain embodiments, the polymer is a carboxyl-terminated poly(ethylene glycol) or succinimide-terminated poly(ethylene glycol) which can react with amine-terminated EGCG to form the conjugate. In alternative embodiments, the polymer is an amine-terminated poly(ethylene glycol) which can react with carboxyl-terminated EGCG or succinimide-terminated EGCG to form the conjugate.

The delivery agent is capable of being formed into a delivery vehicle, thus allowing for the incorporation of a conjugated flavonoid into the delivery vehicle without compromising the biological or pharmacological properties of the flavonoid. As well, the delivery agent should be biocompatible, and may be biodegradable in some embodiments.

The following discussion refers to an embodiment in which the flavonoid is a catechin-based flavonoid and in which the delivery agent is an aldehyde-terminated polymer. However, it will be understood that the aldehyde condensation reaction between an aldehyde-containing chemical group and a flavonoid is applicable to conjugation of any delivery agent having a functional group described above, including following acid treatment of the delivery agent, to any flavonoid.

Thus, the reaction may involve conjugation of a polymer containing a free aldehyde group or a group that is able to be converted to a free aldehyde group, for example, in the presence of an acid to a catechin-based flavonoid.

The catechin-based flavonoid may be used in its monomeric form or dimeric form and it is important to retain the monomeric form or dimeric form of the flavonoid during conjugation so that the conjugation does not result in the formation of oligomers of the flavonoid. As stated above, conjugation of a polymer to a flavonoid results in augmentation of the flavonoid's biological or pharmacological properties.

The polymer may be any polymer having a free aldehyde group prior to conjugation with the catechin-based flavonoid, or having a group that is converted to an aldehyde group in the presence of an acid, for example an acetal group. Furthermore, it will be understood that the polymer should be non-toxic, biocompatible and suitable for pharmacological use. The polymer may also have other desirable properties. For example, the polymer may have low immunogenicity, and it may be biodegradable or non-biodegradable depending on the desired biological application of the composition, for example, for controlled release of catechin-based flavonoids and the anti-cancer agent at a particular site in a body.

The polymer may be chosen based on its particular characteristics and its ability to form certain types of delivery vehicles. For example, the polymer may be an aldehyde-terminated poly(ethylene glycol). Alternatively, the polymer may be an aldehyde-derivatized hyaluronic acid, hyaluronic acid aminoacetylaldehyde diethylacetal conjugate, aldehyde-derivatized hyaluronic acid-tyramine, hyaluronic acid aminoacetylaldehyde diethylacetal conjugate-tyramine, cyclotriphosphazene core phenoxymethyl(methylhydrazono) dendrimer, or thiophosphoryl core phenoxymethyl (methylhydrazono) dendrimer. The polymer may also be any biological polymer, modified to contain a free aldehyde group or a group that is convertible to an aldehyde in the presence of an acid, for example an aldehyde-modified protein, peptide, polysaccharide or nucleic acid. In one particular embodiment, the polymer is an aldehyde-terminated poly(ethylene glycol) (PEG-CHO). PEG is particularly chosen to form the conjugate because PEG is a polymer widely used as a pharmacological ingredient, and possesses good hydrophilic, non-toxic, non-immunogenic and biocompatibility characteristics with low biodegradability.

The free aldehyde group on the polymer allows for the conjugation of the polymer in a controlled manner to either the C6 or the C8 position of the A ring, or both, of the flavonoid structure, thus preventing disruption of the flavonoid structure, particularly the B and C rings of the flavonoid, and thus preserving the beneficial biological and pharmacological properties of the flavonoid. While the C6 and C8 positions are most preferred, it will be apparent to a person skilled in the art that other conjugation positions of the flavonoid (e.g. at other rings) are also possible.

The polymer is conjugated to the catechin-based flavonoid via a reaction of the aldehyde group of the polymer with the C6 and/or the C8 position of the A ring of the catechin-based flavonoid.

The conjugate is synthesized using acid catalysis of a condensation of the aldehyde group of the polymer with the catechin-based flavonoid, or using acid to convert a functional group on the polymer to a free aldehyde prior to condensation of the aldehyde group with the catechin-based flavonoid.

To conjugate the polymer and the catechin-based flavonoid, the polymer and the catechin-based flavonoid may be separately dissolved in a suitable solvent. The polymer with the free aldehyde is added, for example by dropwise addition, to the solution containing the catechin-based flavonoid, in the presence of an acid. The reaction is allowed to go to completion. Following the conjugation reaction, excess unreacted polymer or catechin-based flavonoid can be removed from the conjugated composition, for example by dialysis or by molecular sieving.

A conjugate of a polymer containing a free aldehyde and a catechin-based flavonoid, having the polymer conjugated at the C6 and/or the C8 position of the A ring of the flavonoid is also contemplated.

Conjugation of the polymer also allows for the incorporation of catechin-based flavonoids into various compositions or vehicles. By selection of the particular polymer containing a free aldehyde group based on the physical properties of the polymer, it is possible to incorporate flavonoids into a variety of different vehicle types, allowing for the delivery of high concentrations of flavonoids in different contexts to various targeted areas of the body.

Thus, the conjugate resulting from the above-described reaction may be formed into a delivery vehicle, depending on the nature of the polymer portion of the conjugate. The delivery vehicle may be used to deliver the catechin-based flavonoid to a body, including a particular targeted site in a body, depending on the nature of the delivery vehicle.

The conjugate, delivery vehicle, anti-cancer agent delivery vehicle or the pharmaceutical composition comprising any of these are of nanometer dimentions wherein the chemical moiety and the at least one flavonoid are of nanometer dimentions.

The anti-cancer agent may be any agent that has an anti-cancer effect on a cell, including an anti-tumour effect, such as a cytotoxic, apoptotic, anti-mitotic anti-angiogenesis or inhibition of metastasis effect. The anti-cancer effect is intended to include inhibition or reduction of tumour cell growth, inhibition or reduction of carcinogenesis, killing of tumour cells, or inhibition or reduction of carcinogenic or tumourogenic properties of a cell, including a tumour cell.

An anti-cancer agent includes a protein, a nucleic acid, a small molecule or a drug. An anti-cancer agent that is a protein may be a peptide, an antibody, a hormone, an enzyme, a growth factor, or a cytokine. An anti-cancer agent that is a nucleic acid may be single stranded or double stranded DNA or RNA, a short hairpin RNA, an siRNA, or may comprise a gene encoding an anti-cancer product. Also included in the scope of anti-cancer agent is a chemotherapeutic agent or an angiogenesis inhibitor. The anti-cancer agent may be an antibody, including a monoclonal antibody, directed against a tumour cell-surface marker, an immunoregulatory peptide, a cytokine or a growth factor. The anti-cancer agent may be Herceptin (trastuzumab) or TNP470 (N-(2-Chloroacetyl)carbamic acid (3R,4S,5S,6R)-5-Methoxy-4-[(2R,3R)-2-methyl-3-(3-methyl-2-buten-1-yl)-2-oxiranyl]-1-oxaspiro[2.5]oct-6-yl ester) an analog of fumagillin, doxorubicin, cisplatin, paclitaxel, daunorubicin, or a mixture thereof.

The anti-cancer agents may include tyrosine kinase inhibitors, or cisplatin, platinum, carboplatin, gemcitabine, paclitaxel, docetaxel, etoposide, vinorelbine, topotecan, or irinotecan. Enzymes inducing apoptosis may include TRAIL-R1, TRAIL-R2 or FasL. Nucleic acid anti-cancer agents may include plasmid DNA (encoding therapeutic proteins) or antisense oligonucleotides (ODNs) or small interfering RNA (siRNA). ODN is a short single stranded DNA, which is complementary to the transcribed mRNA (sense sequence), and hence can bind to this mRNA and prevent it from being translated into the protein inside the cells. Alternatively, ODNs can be targeted to bind to a splicing site of a pre-mRNA, and aimed to modify the exon end of the mRNA. siRNA, on the other hand, is a short double or single stranded RNA, which assembles into endoribonuclease-containing complexes upon entering cells, also known as RNA-induced silencing complex (RISC). These siRNA molecules then unwind inside the RISC, making the complex activated to recognize and splice its mRNA target strands in the cells, and thus down-regulating the expression of the target protein. Similarly micro-RNA capable of inducing apoptosis may be initiated by a specific micro-RNA. The micro-RNA may include: MiR-15, MiR-16, MiR-99a/let7c/MiR-125b2 or other suitable pro-apoptotic micro-RNA.

The biological activity of the anti-cancer agent is temporarily partially or completely masked while incorporated into the present delivery vehicles, making them less available while the anti-cancer agent is assembled in the delivery vehicle, meaning that the anti-cancer agent is not able to exert anti-cancer activity or interact with other molecules in a bioactive manner while contained in the delivery vehicle, and is also protected from activity of other molecules. Upon release of the anti-cancer agent from the delivery vehicle, the biological properties of the anti-cancer agent are once again available, and the anti-cancer agent is able to exert an anti-cancer effect once delivered to the cell.

In one embodiment an anti-cancer agent is loaded into the conjugate or delivery agent. The anti-cancer agent may be loaded or encapsulated in the conjugate or anti-cancer delivery vehicle through hydrophobic interactions and/or Π-Π stacking interactions with the flavonoid.

The drug loading of the anti-cancer agent in the delivery agent of the invention is preferably more than other known loading of drugs in delivery agents. Drug loading is defined as the weight percentage of the anti-cancer agent in the delivery vehicle, while drug loading efficiency is defined as the weight percentage of the entrapped anti-cancer agent compared to the free anti-cancer agent introduced initially, as described in the examples. The drug loading may be increased by 1.5 to 5 times the reported range of drug loading. Preferably the drug loading is increased by 1.75 to 4.25 times the reported range of drug loading. In the case of antibodies and siRNA where drug loading is not so well established we have demonstrated that a polypeptide and a nucleic acid is not only able to be successfully loaded into the delivery agent but can also be successfully delivered in vivo and in vitro.

The ratio of drug to conjugate can range from 6:1 to 1:6. In particular embodiment's ratios of doxorubicin to PEG/EGCG were successful at ratios of 6:1, 4:1, 2:1 1:1, and 1:2. Preferably the amount of anti-cancer agent is greater than the amount of conjugate provided the anti-cancer agent is able to form an interaction with the flavonoid.

EXAMPLES (−)-Epigallocatechin gallate (EGCG), a main ingredient of green tea, exhibits numerous biological and pharmacological effects. In the following examples, conjugates of poly(ethylene glycol) with EGCG were synthesized using aldehyde-mediated condensation by an acid catalyst.

Figure 1:
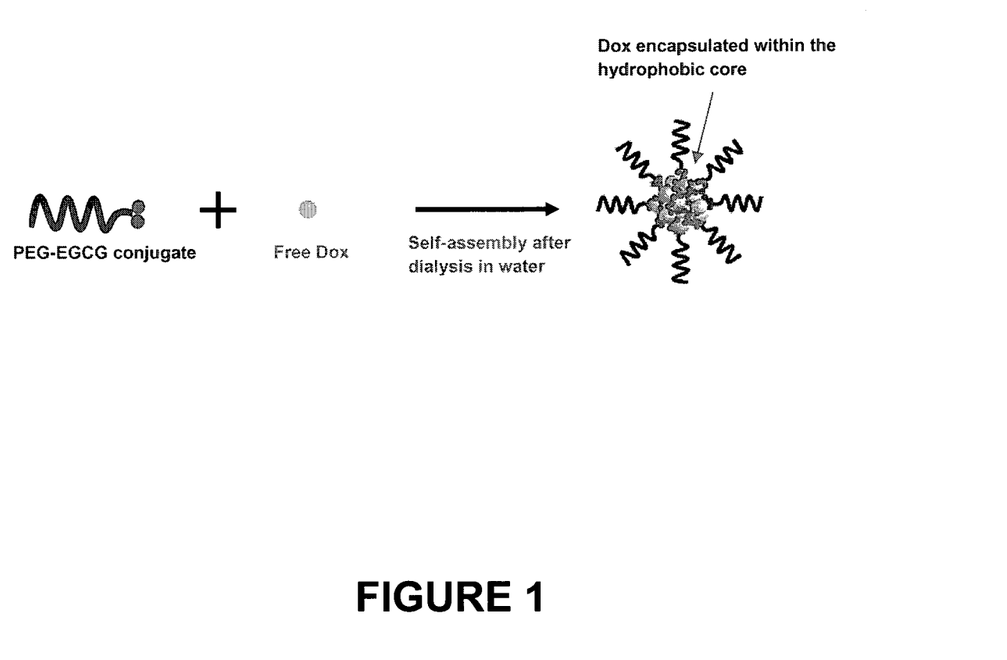
FIG. 1 shows a scheme illustrating the self-assembly of poly ethylene glycol/(−)-epigallocatechin gallate (PEG-EGCG) conjugates loaded with doxorubicin.

Example 1: Formation of Delivery Vehicle Comprising Doxorubicin and PEG-EGCG Conjugates In one embodiment, the drug molecule is doxorubicin ("Dox" for short). FIG. 1 shows a scheme illustrating the self-assembly of PEG-EGCG conjugates loaded with Dox to form the delivery vehicle. In this embodiment, the delivery vehicle is in the form of a micelle. It is based on the self-assembly of PEG-EGCG conjugates into micelles in aqueous environment, stemming from the hydrophilic nature of the PEG chain of the PEG-EGCG conjugate. Due to the similarity in the multi-ring structures of the EGCG moiety and Dox, the EGCG moiety is designed to encapsulate Dox through the hydrophobic interactions and π-π stacking interactions. Dox was successfully encapsulated within the delivery vehicles by simple mixing and dialysis. Advantageously, It is found that the delivery vehicles demonstrate exceptionally high DoX loading in comparison to other delivery vehicles systems (e.g. polymeric micellar systems) known in the prior art. Dynamic light scattering (DLS) measurements also showed that the dimensions of the delivery vehicles are ideal for passive tumor targeting via EPR effect.

Figure 2:
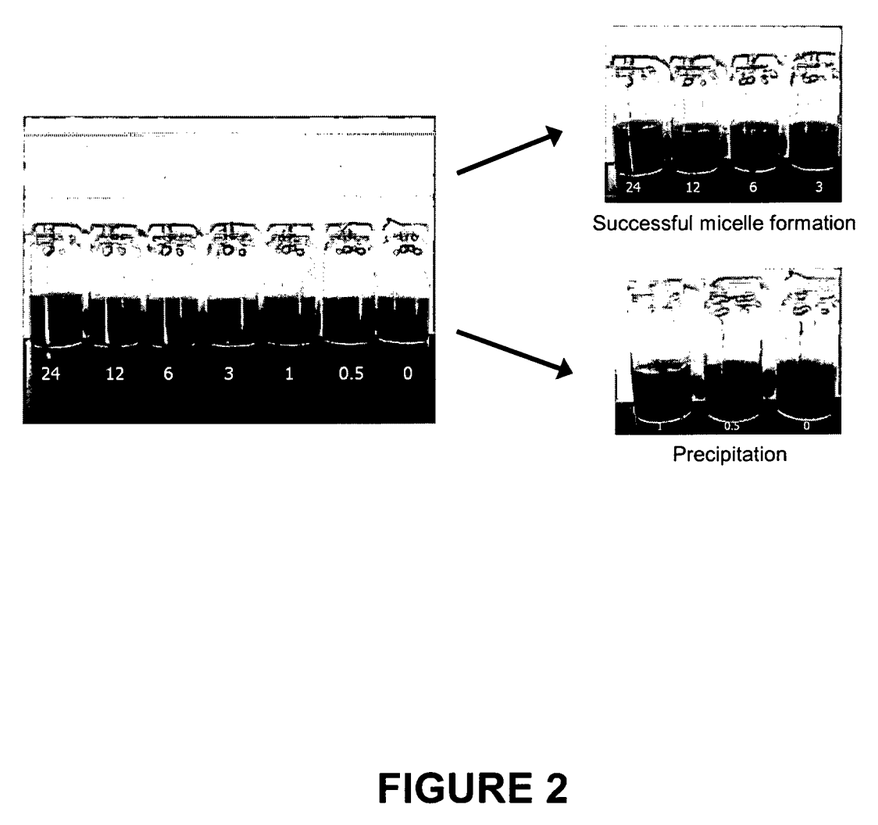
FIG. 2 demonstrates the formation of PEG-EGCG conjugates loaded with doxorubicin at varying initial PEG-EGCG concentrations. The numeral reference below each bottle sample represents the initial PEG-EGCG concentration in mg/ml.

In this example, the delivery vehicle was prepared by dialysis of a mixture of PEG-EGCG conjugates and Dox dissolved in organic solvent dimethylformamide (DMF) against distilled water. Different concentrations of PEG-EGCG conjugates (0, 0.5, 1, 3, 6, 12, 24 mg/ml, respectively) were used to encapsulate a fixed concentration of Dox at 12 mg/ml. During the dialysis, the gradual replacement of the organic solvent with water triggered the self-assembly of the delivery vehicles and the entrapment of Dox within the assembled structures. As shown in FIG. 2, precipitates were obtained during the dialysis when PEG-EGCG concentrations of 0, 0.5 and 1 mg/ml were used, indicating ineffective delivery vehicle formation. In contrast, with PEG-EGCG concentrations of 3, 6, 12 and 24 mg/ml, homogeneous solutions were achieved, demonstrating the successful encapsulation of Dox within the delivery vehicles. This example indicated that a suitable ratio of Dox to PEG-EGCG conjugates should be carefully selected in order for the Dox/PEG-EGCG delivery vehicles to self-assemble effectively.

Experimental

Materials:

Aldehyde-terminated PEG (PEG-CHO, Mw 5000) was purchased from NOF Co., Japan. EGCG was purchased from Kurita Ltd., Japan. Doxorubicin hydrochloride (Dox.HCl) was obtained from Boryung Pharmaceuticals Inc., Korea.

Synthesis of PEG-EGCG Conjugate:

The aldehyde-terminated PEG (0.35 g) and EGCG (0.65 g) were separately dissolved in a mixture of acetic acid, water and dimethyl sulfoxide (DMSO). The reaction was started with the dropwise addition of the PEG-CHO solution at 20° C. (pH 2) under a nitrogen atmosphere for 48 h. The resulting products were dialyzed (molecular weight cut-off (MWCO)=3500) and lyophilized to give the PEG-EGCG conjugate.

Synthesis of Delivery Vehicle:

Dox.HCl (12 mg, 21 μmol) was dissolved in 1 ml of DMF. Triethylamine (29 μl, 210 μmol) was then added to the solution to neutralize the hydrochloride. Next, PEG-EGCG conjugates (1 ml) with different concentrations dissolved in DMF were added to the solution, and the resulting mixtures were vortexed for 20 min. Each sample solution was then transferred to dialysis tubes with a MWCO of 3500 Da. The tubes were dialyzed against distilled water for 2 days, with the water replaced every 12 h. The sample solutions were lyophilized to obtain solid micelles.

Determination of Drug Loading:

The absorbance of the sample solutions was measured at 480 nm using a Hitachi U2810 UV-Vis spectrophotometer after the dried samples were dissolved in DMF. The amount of Dox in each sample was estimated by comparing to the Dox standards. Drug loading was calculated from the amount of Dox in the delivery vehicles, and the weight of the dried delivery vehicles samples.

Determination of Delivery Vehicle Size:

The size of the delivery vehicle samples was determined by DLS using a Brookhaven 90Plus Particle Size Analyzer. Each sample solution was prepared using distilled water to give 10 μg/ml of Dox before conducting the DLS measurements at 25° C.

Results: Characteristics of the Delivery Vehicle

The characteristics of the delivery vehicle of Example 1 are summarized in Table 1 below. Drug loading is defined as the weight percentage of Dox in the delivery vehicle, while drug loading efficiency is defined as the weight percentage of the entrapped Dox compared to the free Dox introduced initially. The samples with initial PEG-EGCG concentrations of 3 and 6 mg/ml showed an extraordinarily high drug loading of 85 and 68 wt %, respectively. The highest Dox loading achieved (85 wt %) corresponded to more than 4 times the average Dox loading (10-20 wt %) in the block copolymeric delivery vehicles developed by other groups (H. M. Aliabadi et al, *Expert Opinion on Drug Delivery*, 2006, 3, 139-162). Without being limited to any particular mechanism it is hypothesized that such a high drug loading is possibly due to the strong hydrophobic interaction and/or π-π stacking interactions between the EGCG moiety and Dox, which would possibly enhance the encapsulation of Dox in the self-assembly process, although the EGCG moiety was much smaller than the hydrophobic chain of other PEG block copolymers reported.

The size of the delivery vehicles ranged from 78.5 to 192.4 nm (see Table 1). The size increased as the drug loading increased, but decreased with increasing initial PEG-EGCG concentration. The increase in size should be correlated to the encapsulation efficiency since the EGCG moiety played a key role in encapsulating Dox. Thus, it is expected that not only the size, but also the drug release profile and the stability of delivery vehicles, which are important aspects for any targeted drug delivery system, could be controlled by the initial PEG-EGCG concentration introduced. The nanometer dimensions of the delivery vehicles (less than 200 nm) conferred the ability of targeting tumor tissue via EPR effect. At the same time, they enabled prolonged blood residence time, as they helped to avoid opsonization and renal clearance of delivery vehicles.

TABLE 1

Characteristics of PEG-EGCG Conjugates Loaded with Dox in Accordance with an Embodiment of the Present Invention

| Samples | Initial PEG-EGCG concentration (mg/ml) | Initial Dox concentration (mg/ml) | Average hydrodynamic diameter (nm)* | Drug loading efficiency (wt %) | Drug loading (wt %) |
|---|---|---|---|---|---|
| 1 | 3 | 12 | 192 | 60 | 85 |
| 2 | 6 | 12 | 129 | 77 | 68 |
| 3 | 12 | 12 | 115 | 77 | 49 |
| 4 | 24 | 12 | 79 | 79 | 35 |

*Determined by DLS measurements.

Figure 3:
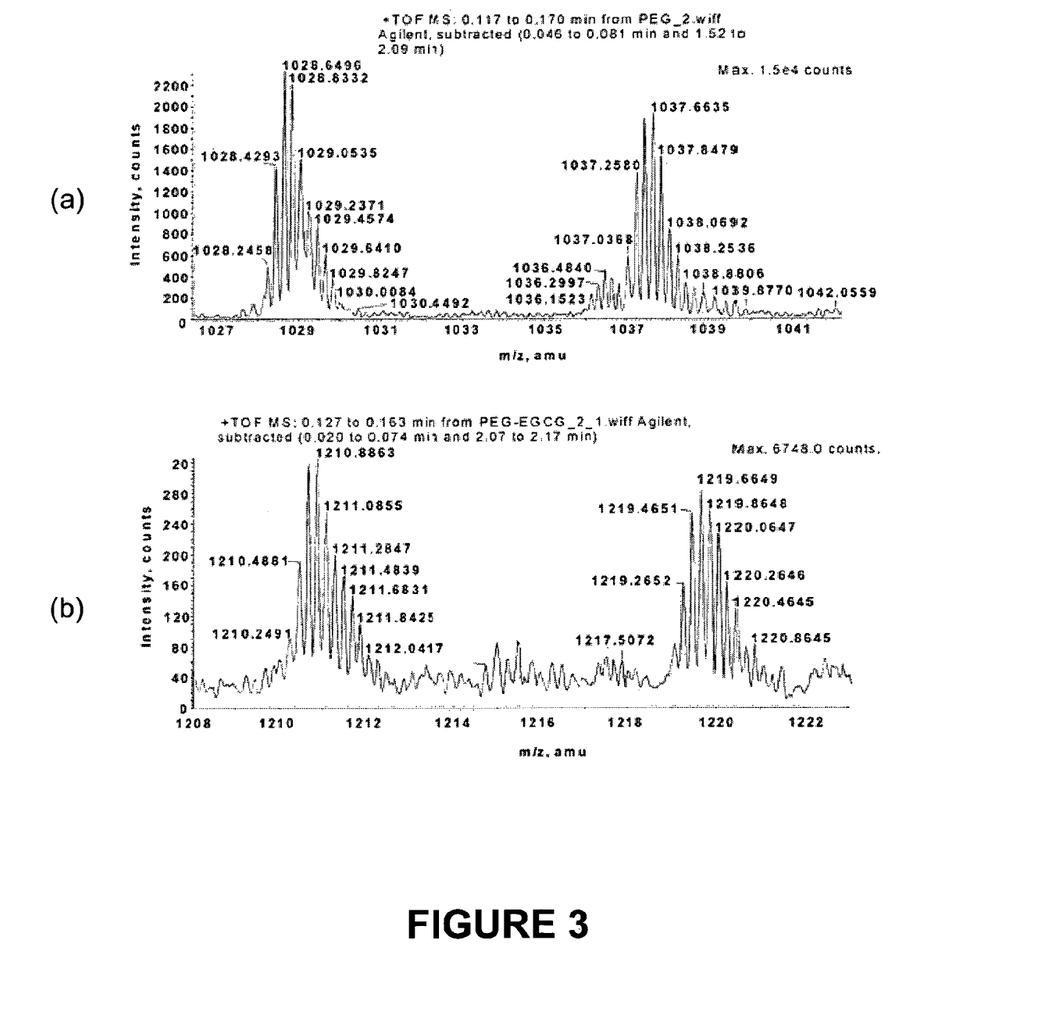
FIG. 3 shows the electrospray ionization time-of-flight mass spectra of (a) PEG and (b) PEG-EGCG, respectively.

The electrospray ionization time-of-flight (ESI-TOF MS) mass spectra of (a) PEG and (b) PEG-EGCG, respectively, are shown in FIG. 3. The m/z difference between two clusters of peaks was observed as a PEG repeating unit of 44 for both PEG and PEG-EGCG taking account of a charge of +5 calculated from 0.2 m/z difference between each peak (e.g. (1037.26−1028.43)×5=44.15). However, the peaks of PEG-EGCG shifted higher with molecular weight of two EGCG (e.g. (1211.09−1028.65)×5=912.36) compared to those of PEG, demonstrating that the PEG-EGCG conjugate comprises two repeating units of EGCG bound to one end of the PEG chain, i.e. each repeating unit of EGCG remains monomeric after conjugation and no oligomers of EGCG were formed. Although in this embodiment two monomeric flavonoids (EGCG) conjugated to one end of the chemical moiety (PEG) has been demonstrated, it is to be understood and appreciated that other conjugate configurations, such as three monomeric flavonoids conjugated to one end of the chemical moiety, or one or more dimeric flavonoids conjugated to one end of the chemical moiety, are also contemplated.

Figure 4:
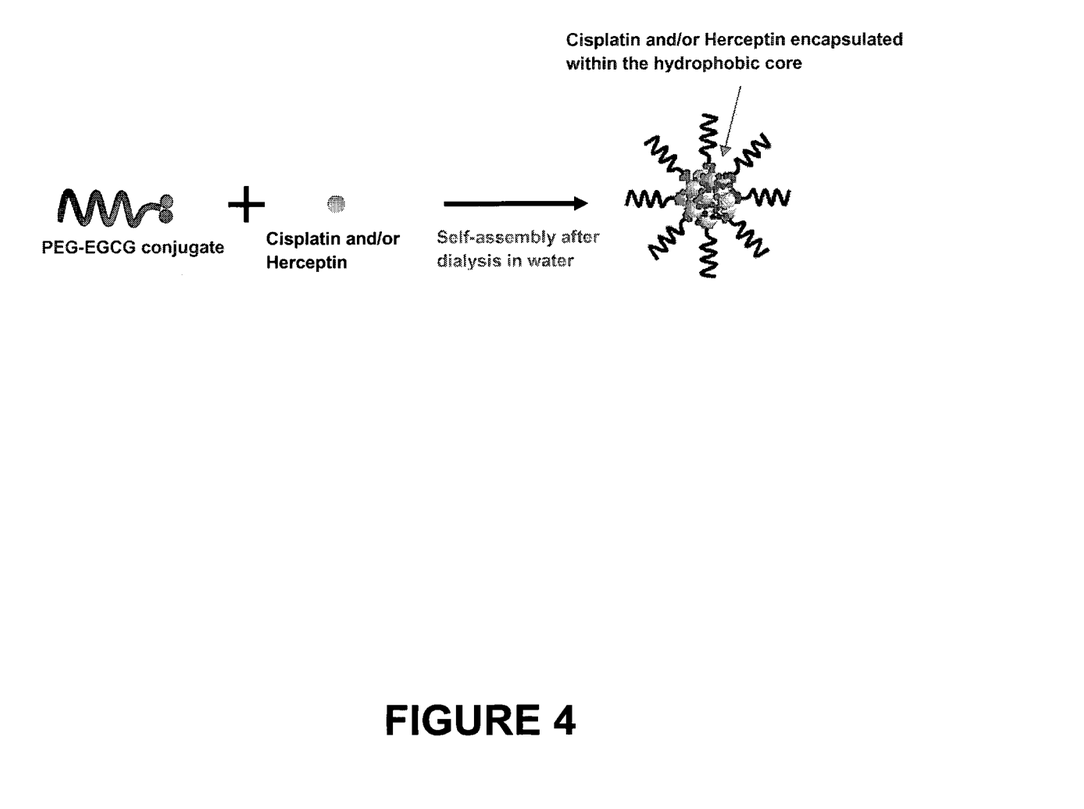
FIG. 4 shows a scheme illustrating the self-assembly of PEG-EGCG conjugates loaded with cisplatin and/or herceptin.

Example 2: Formation of Delivery Vehicle Comprising Cisplatin and PEG-EGCG Conjugates In another embodiment, the drug molecule is cisplatin. FIG. 4 shows a scheme illustrating the self-assembly of PEG-EGCG conjugates loaded with cisplatin to form the delivery vehicle. In this embodiment, the delivery vehicle may be in a form of a chelate-complex. The interaction between cisplatin and the PEG-EGCG conjugates is probably due to the chelation of Pt (platinum) by the OH- moieties of the EGCG. The chelate-complex is formed as a consequence of the chelation where the PEG-EGCG conjugates cluster around the central cisplatin, thereby confining cisplatin therein.

In this example, the cisplatin/PEG-EGCG complex was prepared by dialysis of a mixture of PEG-EGCG and cisplatin dissolved in (i) water or (ii) organic solvent dimethylformamide (DMF) against distilled water. Different concentrations of PEG-EGCG conjugates (1.2, 2.4, 6, and/or 12 mg/ml) were used against a fixed concentration of cisplatin at 1.2 mg/ml. During the dialysis, the PEG-EGCG conjugates cluster around the central cisplatin to confine cisplatin within the cluster.

Experimental

Materials:

Aldehyde-terminated PEG (PEG-CHO, Mw 5000) was purchased from NOF Co., Japan. EGCG was purchased from Kurita Ltd., Japan. Cisplatin [cis-dichlorodiamminoplatinum(II); CDDP] was purchased from Sigma-Aldrich Pte. Ltd., Singapore.

Synthesis of PEG-EGCG Conjugate:

The PEG-EGCG conjugates were synthesised as described in Example 1. Alternatively, the polymer may be a carboxyl-terminated poly(ethylene glycol) which can react with amine-terminated EGCG to form the conjugate, the synthesis of which is apparent to persons skilled in the art.

Synthesis of Delivery Vehicle:

CDDP (1.2 mg, 4 μmol) was dissolved in 1 ml of water or DMF. PEG-EGCG conjugates (1 ml) with different concentrations dissolved in water or DMF were added to the solution, and the resulting mixtures were vortexed for 20 min. Each sample solution was then transferred to dialysis tubes with a MWCO of 1000 Da. The tubes were dialyzed against distilled water for 2 days, with the water replaced every 12 h. The delivery vehicles were then harvested.

Determination of Drug Loading:

The absorbance of the sample solutions was measured at 280 nm using a Hitachi U2810 UV-Vis spectrophotometer for the PEG-EGCG content. The amount of cisplatin in each sample was measured by PelkinElmer SCIEX ICP Mass Spectrometer Elan DRC II. Drug loading efficiency was calculated from the amount of cisplatin confined in the delivery vehicle, and the amount of the cisplatin added into the system initially. Drug loading was calculated from the amount of cisplatin in the delivery vehicle, and the weight of the delivery vehicle.

Determination of Delivery Vehicles Size:

The determination protocol is the same as that described in Example 1.

Results

The characteristics of the PEG-EGCG conjugates with cisplatin dissolved in (i) water and (ii) DMF are summarized in Table 2 and Table 3, respectively. Drug loading is defined as the weight percentage of cisplatin in the delivery vehicle, while drug loading efficacy is defined as the weight percentage of the confined cisplatin compared to the free cisplatin introduced initially. Samples with increasing PEG-EGCG concentration showed an increasing trend of drug loading efficiency.

Dynamic light scattering (DLS) measurements also showed that the dimensions of the delivery vehicle were in the range of 153 to 194 nm (see Table 2 and Table 3) which are ideal for passive tumor targeting via EPR effect. The nanometer dimensions of the delivery vehicle (less than 200 nm) conferred the ability of targeting tumor tissue via EPR effect. At the same time, they enabled prolonged blood residence time, as they helped to avoid opsonization and renal clearance of the delivery vehicle.

TABLE 2

Characteristics of PEG-EGCG Conjugates Loaded with Cisplatin in Water in Accordance with an Embodiment of the Present Invention

| Samples | Initial PEG-EGCG concentration (mg/ml) | Initial Cisplatin concentration (mg/ml) | Average hydrodynamic diameter (nm)[a] | Drug loading efficiency (wt %)[b] | Drug loading (wt %)[c] |
|---|---|---|---|---|---|
| 1 | 1.2 | 1.2 | 153 | 3.1 | 3.8 |
| 2 | 2.4 | 1.2 | 141 | 4.3 | 3.0 |
| 3 | 6 | 1.2 | 194 | 8.9 | 2.0 |

[a]Determined by DLS measurements.
[b]Weight percentage of cisplatin loaded over one in feed (by ICP-MS).
[c]Weight percentage of cisplatin loaded over total delivery vehicle (by ICP-MS and UV/Vis)

TABLE 3

Characteristics of PEG-EGCG Conjugates Loaded with Cisplatin in DMF in Accordance with an Embodiment of the Present Invention

| Samples | Initial PEG-EGCG concentration (mg/ml) | Initial Cisplatin concentration (mg/ml) | Average hydrodynamic diameter (nm)[a] | Drug loading efficiency (wt %)[b] | Drug loading (wt %)[c] |
|---|---|---|---|---|---|
| 1 | 1.2 | 1.2 | 132 | 1.8 | 2.2 |
| 2 | 2.4 | 1.2 | 131 | 2.7 | 1.4 |
| 3 | 6 | 1.2 | 119 | 3.1 | 0.69 |
| 4 | 12 | 1.2 | 130 | 4.9 | 0.52 |

[a]Determined by DLS measurements.
[b]Weight percentage of cisplatin loaded over one in feed (by ICP-MS).
[c]Weight percentage of cisplatin loaded over total delivery vehicle (by ICP-MS and UV/Vis)

Figure 5:
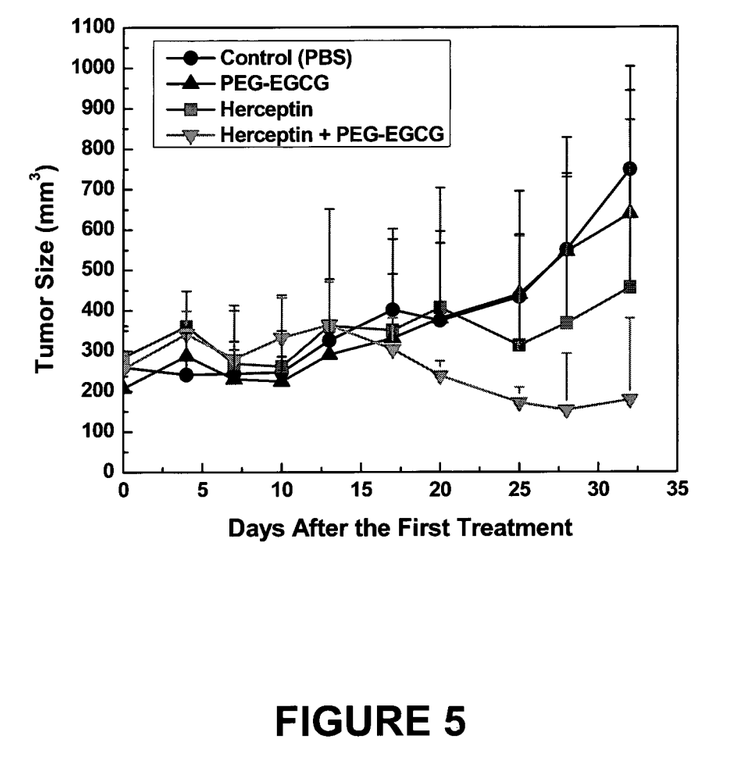
FIG. 5 shows the in-vivo HER2-overexpressed human breast cancer cell (BT-474) xenograft to Athymic Nude-Foxn1 nu (n-6) with PEG-EGCG conjugates loaded with herceptin.

Example 3: Test Results of Using Delivery Vehicle Comprising Herceptin and PEG-EGCG Conjugates The present inventors have also successfully encapsulated herceptin (Herceptin being purchased from Roche, Switzerland) within PEG-EGCG conjugates following the synthesis route outlined in Example 2 above. The conjugates have shown enhanced anti-cancer effect on BT-474 HER2/neu overexpressed breast cancer xenograft, as shown in FIG. 5.

Results

In-Vivo Anti-Cancer Efficacy of Delivery Vehicle:

Athymic (nu/nu) mice (5-6 weeks old) were purchased from the Harlan, UK and all animal experiments were performed in compliance with Institutional Animal Care and Use Committee (IACUC) procedures and guidelines. A 17β-estradiol pellet (Innovative Research of America) was inserted subcutaneously (s.c.) into each mouse 1 day before injection with BT-474 cells ($1 \times 10^7$ cells in 100 µl phosphate-buffered saline (PBS) with 120 µl matrigel (BD Bioscience)) s.c. at the right flank. Tumor volume V (mm³) was determined by measuring length l and width w and calculating volume ($V=lw^2/2$) as described (W. P. McGuire et al, *N. Engl. J. Med.* 1996, 344(1), 1268). Experimental and control treatments were carried out once the tumors achieved a mean size of 250 mm³. Mice were randomized to different groups (n=6) before starting the various treatments. Herceptin used was 2.5 mg/kg and PEG-EGCG was 100 µM. Treatments were administered twice per week. Sixteen days later, the animals were injected with vehicle (PBS) (●), PEG-EGCG (▲), herceptin (□), (herceptin+PEG-EGCG) micelle (▼). The results were reported as mean±standard deviation.

The enhanced anti-cancer effect on BT-474 HER2/neu overexpressed breast cancer xenograft could be due to the accumulation of the delivery vehicles at the tumor site and hence reduced the tumor size significantly as compared to the animal groups treated with herceptin only. The mechanism for the encapsulation of herceptin within the delivery vehicle may be similar to that contemplated in Example 1, i.e. the EGCG moiety encapsulates herceptin through the hydrophobic interactions and π-π stacking interactions between the proline residues and the EGCG moiety.

In conclusion, the present delivery vehicles overcome the challenge of low drug to loading faced by the conventional drug delivery vehicles (such as polymeric micellar carriers) comprising of a variety of block copolymers as mentioned in previous paragraphs. Unlike the existing prior art delivery vehicles, which utilize long hydrophobic polymer chains, the present delivery vehicles provide strong drug interactions via the EGCG moiety to achieve high drug loading. The enhanced encapsulation or confinement capability of the present delivery vehicles may also be extended to other anti-cancer drugs without any modification of their structure and hence makes it a potential system for co-delivery of multi anti-cancer agents, such as herceptin and doxorubicin or paclitaxel and daunorubicin.

Unique properties of the present delivery vehicles which make them particularly suitable for use in cancer therapy include (i) their nanometer-dimensions of between 10 and 200 nm; (ii) their amphiphilic structure that confers increased solubility in water; and (iii) their ability to encapsulate or confine anti-cancer agents within its inner core. The design of a delivery vehicle with a higher drug loading is important towards achieving an efficient cancer therapy. It is also expected that such a delivery vehicle would minimize the side effects caused by the potential unspecific drug delivery as the dose of the delivery vehicle may be reduced. Furthermore, having carriers with a higher anti-cancer drug loading reduces the frequency of injections, thereby improving the compliance of patient and reducing trauma caused to the patient. The present delivery vehicles are designed to provide for such unique properties.

Example 4: In Vitro Imaging of siRNA Delivery and Subcellular Localization

Cells were seeded in Lab-Tek™ 8-well chambered coverglasses (Nunc, USA) at a density of $1 \times 10^4$ cells/coverglass. Two days after plating, the culture medium was removed and PEG-EGCG/siRNA transfection complexes were added to the chambered coverglasses. Complexes were prepared as described above by adding varying concentrations of PEG-EGCG to 50 nM Silencer® Cy™3-Labeled Negative Control #1 siRNA (Ambion, USA). After 1, 4 and 24 hours of incubation respectively, cells were washed with Dulbecco's Phosphate-Buffered Saline (DPBS) and fixed with 4% paraformaldehyde (PFA) for 20 minutes at room temperature. After a subsequent wash with DPBS, the cells were stained with 4',6-diamidino-2-phenylin (DAPI, Invitrogen, USA) before being examined by confocal microscopy. Confocal laser scanning microscopy was carried out using an Olympus 1×71 laser scanning microscope using two lasers [excitation max=345 nm, emission max=458 nm for DAPI, excitation max.=547 nm, emission max.=563 nm for Cy3]. The images were acquired using FLUOVIEW software (Olympus, Singapore).

Confocal Microscopic Observation of siRNA Localization

Prior to evaluating the capacity of PEG-EGCG as siRNA carriers, the ability of the PEG-EGCG to deliver siRNA into cells was investigated. The effect of different ratio of siRNA to PEG-EGCG on siRNA uptake was examined using different concentrations of PEG-EGCG to 50 nM siRNA. Internalization of the Cy3-labeled negative control siRNA was monitored by confocal microscopy 1, 4 and 24 hours after transfection to determine the optimum time for transfection of siRNA using the PEG-EGCG. The red fluorescence signal associated with the Cy3-labelled siRNA was only detected in cells population 24 hours after transfection.

Figure 6:
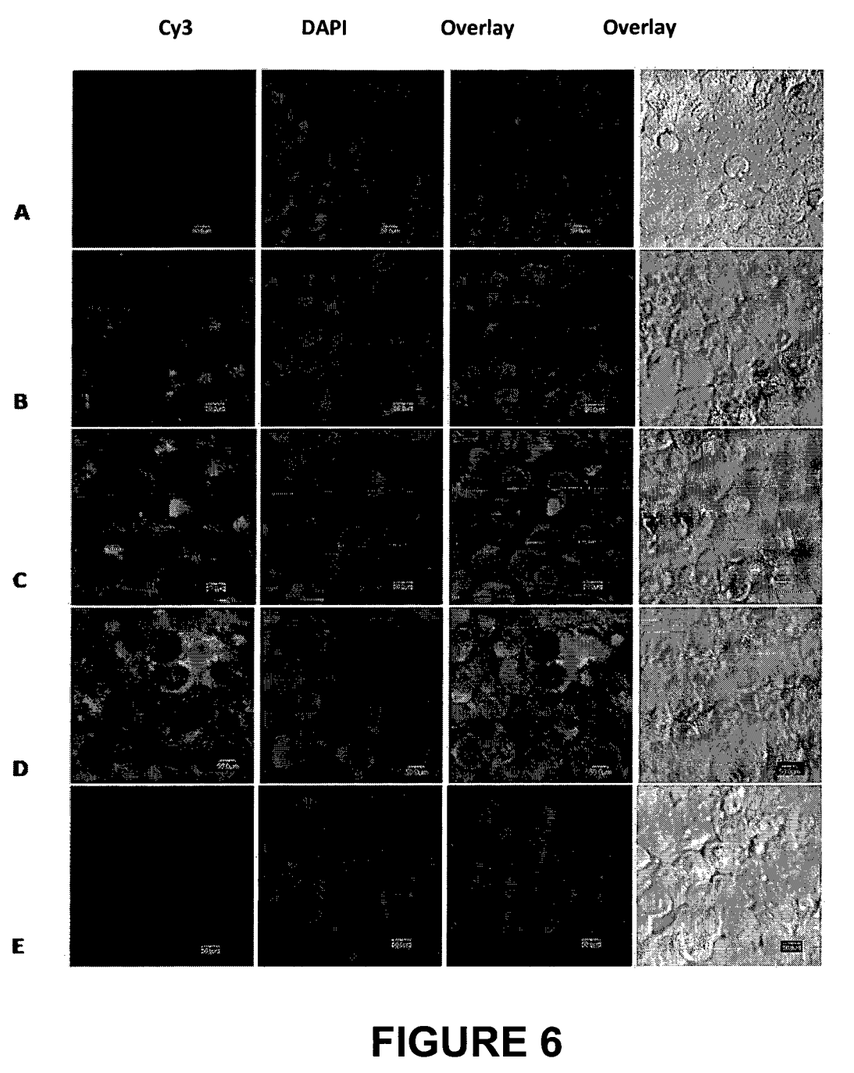
FIG. 6 shows confocal images of Cy3-labeled negative control siRNA (red) counterstained with a nuclei stain, DAPI (Blue) 24 hours after siRNA transfection. siRNA concentration was 50 nM. The overlay images show that the siRNA was localized only in the cytoplasm and not in the nuclei. (A) No PEG-EGCG; (B) 1.5 µg/ml PEG-EGCG; (C) 3.0 µg/ml PEG-EGCG; (D) 6.0 µg/ml and (E) PEG alone.

The confocal images (FIG. 6) showed that PEG-EGCG was able to deliver siRNA into the cells. Moreover, the images reveal a cytoplasmic sublocalization for the siRNA, as seen by overlaying the images of the DAPI stained nucleus and the Cy-3 labelled siRNA. When siRNA was delivered without PEG-EGCG as carriers (FIG. 6A), no fluorescence was observed, demonstrating that siRNA alone was not able to enter the cells. Similarly, when PEG alone was used to complex siRNA (FIG. 6E), no fluorescence was detected, indicating that the red fluorescence, observed in cells transfected with PEG-EGCG/siRNA complexes, was not due to the PEG polymer.

Example 5: Gene Silencing by siRNA Delivered with PEG-EGCG In Vitro

In Vitro Gene Silencing by siRNA—Dual-Luciferase® Reporter Assay (Promega, USA)

To determine whether the siRNA delivered into the cytoplasm by the ODM1 derivatives was functional, we employed the Dual-Luciferase® reporter gene system. In this assay, two reporter enzymes; firefly (*Photinus pyralis*) and *Renilla* (*Renilla reniformis*) luciferases, were simultaneously expressed and their activities measured sequentially from the same cellular sample. The sequence of pGL3 luciferase siRNA is perfectly and uniquely complementary to the firefly luciferase. Therefore, the *Renilla* luciferase expression should not be affected by the siRNA transfection. Hence, the *Renilla* luciferase serves a dual purpose. Firstly, it is a transfection control that can be used to normalize the activity of the firefly luciferase. Secondly, its activity can be monitored to detect any unspecific effect of the siRNA/PEG-EGCG complexes.

Four hours after transfection with pGL3 and pGL4.73 plasmid vectors (Promega, USA), varying concentrations of PEG-EGCG/siRNA complexes (prepared as above) were added to the cells seeded in 96-well plates. Transfections were performed with pGL3 luciferase siRNA (Promega, USA) and Allstars negative control siRNA (QIAGEN, Singapore). After 48 hours, the transfection medium was removed and the cells rinsed with DPBS. Cells were lysed in 50 μl of passive lysis buffer (Promega, USA) and placed on an orbital shaker (Thermoscientific, USA) at room temperature for 15 minutes. Luciferase assay reagent II (LARII) and Stop & Glo® reagent (Promega, USA) used for measuring gene expression were prepared and added to cell lysates following the manufacturer's protocol. Luciferase activity was measured using a Lumat LB9507 luminometer (Berthold, Germany). Transfection efficiency was evaluated as the ratio of the activity of the firefly luciferase (expressed in relative light units (RLU) over the *Renilla* luciferase's activity. For this assay, the effect of 200 nM, 50 nM and 10 nM siRNA on luciferase activity was also investigated.

The ratio of both luciferase was expressed as the relative light units of respectively firefly and *Renilla* (RLU1/RLU2). The ratio obtained in cell population transfected with both luciferases but without siRNA was used to normalize the ratio obtained from various siRNA transfection conditions. A functional siRNA is expected to reduce the levels of the firefly luciferase protein and consequently its activity. The lowered activity will translate in a decrease of the normalized ratio of firefly to *Renilla* luciferase activity. This normalization minimizes experimental variability caused by differences in transfection efficiency or cell viability, thereby allowing more reliable interpretation of the experimental data.

To examine the transfection efficiency of the two plasmid DNA and optimize their ratio, cells were transfected with ratios of *Renilla* to firefly luciferase DNA ranging from 1:10 to 1:400. Indeed, it has been reported that the two promoters used to drive the *Renilla* and firefly luciferase (SV40 and the cytomegalovirus promoters, respectively) could influence each other. The amount of firefly luciferase was maintained constant. Their activities were measured and expressed as a relative ratio.

Figure 7:
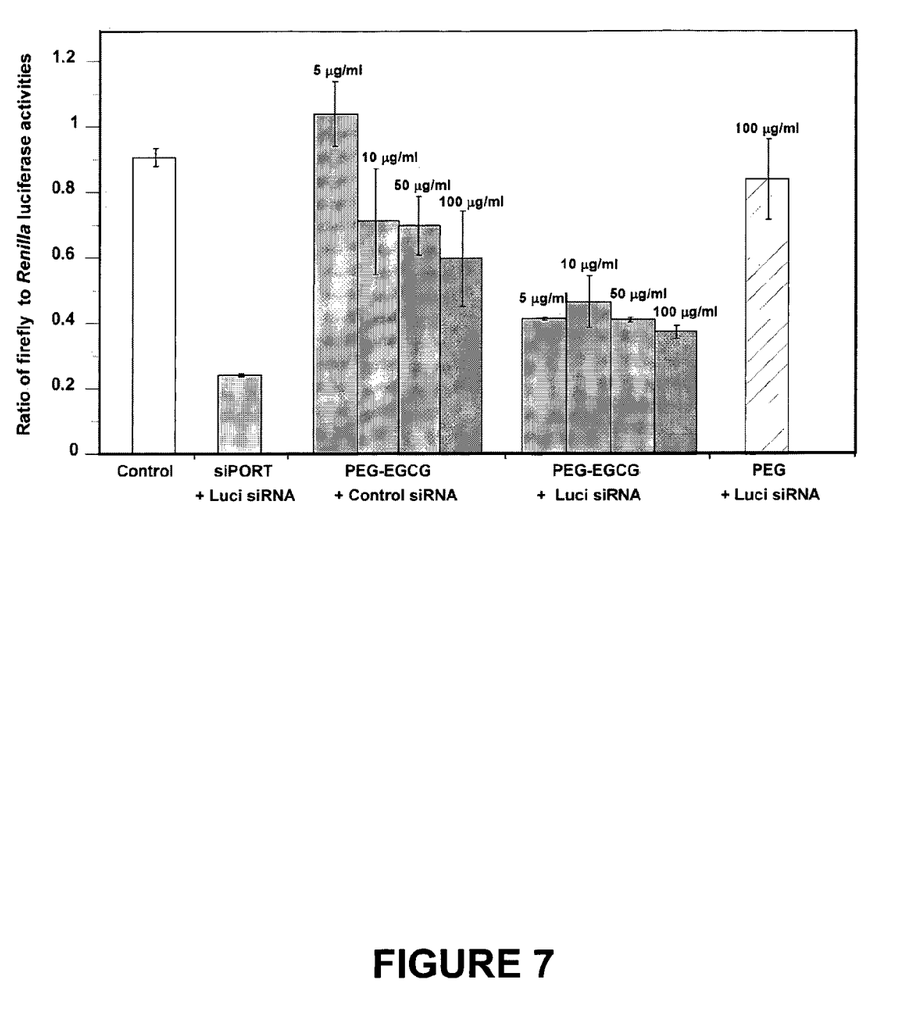
FIG. 7 shows delivery of 200 nM siRNA to pGL3 DNA transfected cells using PEG-EGCG. Ratio of firefly to *renilla* luciferase activities were normalized against cell population transfected only with pGL3 DNA. Control refers to pGL3 DNA transfected cells treated with siRNA alone. siPORT™ is a polyamine-based transfection agent used as a positive control. Luciferase activities were measured 48 hours after transfection without change of medium. Data are means of 3 experiments; S.D. is shown.

When PEG-EGCG was used to complex 200 nM of Luci siRNA, a decrease in the normalized ratio of luciferase activities ranging from 0.55 to 0.62 (FIG. 7) was observed at concentrations of PEG-EGCG from 5 to 100 μg/ml. The most significant decrease was observed at 100 μg/ml of PEG-EGCG. Consistent with the results from confocal microscopy, the PEG carrier alone when mixed with Luci siRNA did not induce a down-regulation of luciferase activity, indicating that PEG by itself could not deliver functional siRNA into cells.

Analysis of Gene Silencing Using Fluorescence Microscopy

To quickly evaluate the functionality and efficiency of siRNA delivered into the cells by PEG-EGCG, cells were transfected with the pEGFP-1 plasmid DNA, encoding the green fluorescent protein. Four hours later, GFP-22 siRNA or control siRNA complexes with either the commercial transfection agent siPORTT™ or with the PEG-EGCG was added to the HCT116 cells. Fluorescence microscopy allowed a rapid visualization of the GFP expressing cells. Any downregulation of GFP by GFP-22 siRNA translated in a decrease of the number of the cells emitting green fluorescence as well as their intensity. GFP-22 siRNA is complementary to 21-bp in the sequence of the GFP's mRNA. FIG. 8A-D showed positive downregulation when GFP-22 siRNA was delivered with siPORT™. The image was used as a positive control in this study.

Cell transfected with pEGFP-1 plasmid vector. (Clontech, USA) were transfected with GFP-22 and Allstars negative control siRNA (QIAGEN, Singapore) 4 hours later using complexes described above. 48 hours later, fluorescence images were taken using Olympus Ix71 fluorescence microscope (Olympus, Singapore). The images were acquired using Image-Pro Plus software (Media-Cybernetics, USA).

Confirming Gene Silencing Using Flow Cytometry

To quantify the downregulation of GFP observed through fluorescence microscopy, flow cytometric analysis of cells transfected with PEG-EGCG/siRNA complexes was performed using the Agilent 2100 bioanalyzer.

48 hours following GFP-22 siRNA transfection into cells already transfected with pEGFP-1 plasmid vector. (Clontech, USA), transfection medium was removed and 50 ul of accutase enzyme cell detachment medium (PAA Laboratories GmbH, Austria) was added per wells. Cells were incubated for 5 minutes; after cells were detached, 150 ul of DPBS was added per well and the contents of the well were transferred into 1.5 ml tubes and spun down at 3000 rpm for 3 minutes. The supernatant was removed and cells were resuspended in cell fluorescence buffer from the Agilent Cell Fluorescent LabChip® Kit (Agilent Technologies, Singapore) at a density of $2.5 \times 10^6$ cells/ml. Cell chip was then loaded with sample and prepared following manufacturer's protocol using reagents provided in the Agilent Cell Fluorescent LabChip® Kit. Flow cytometric analysis was carried out using the Agilent 2100 bioanalyzer (Agilent Technologies, Singapore) and approximately 1000-1200 cell events were counted per sample.

Figure 8:
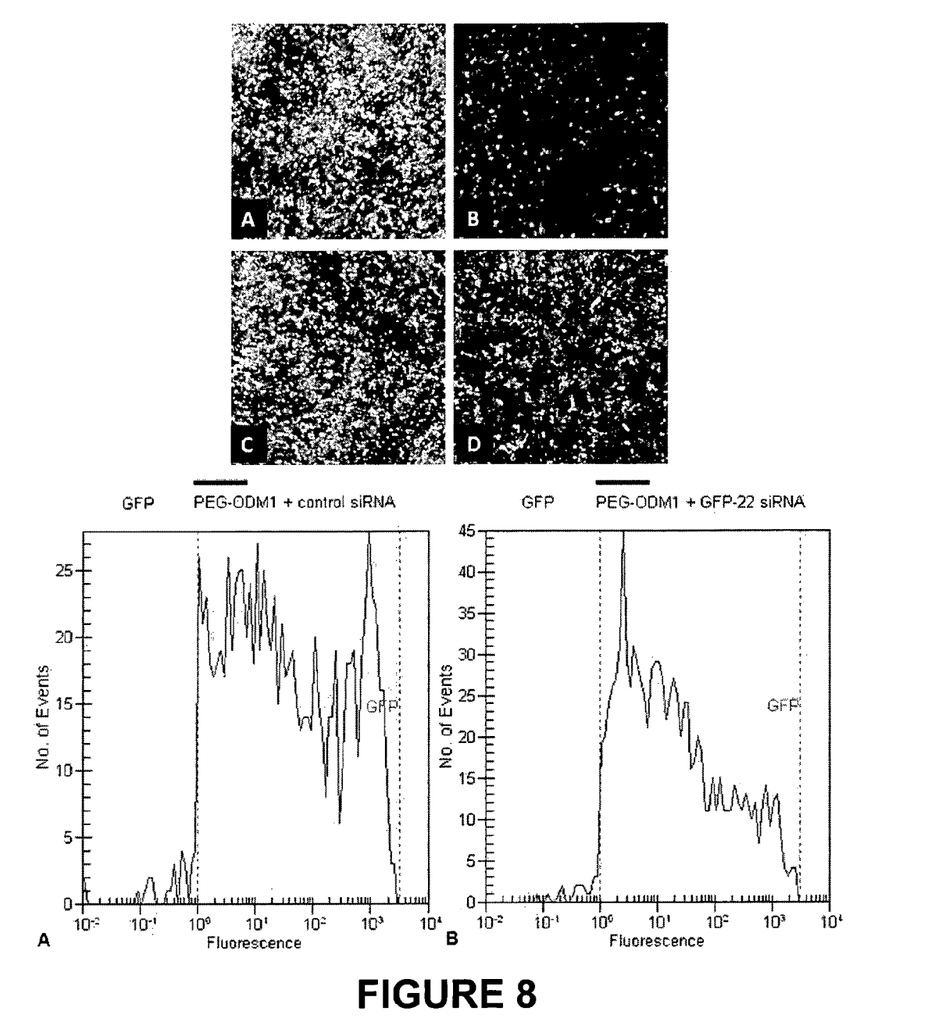
FIG. 8 shows fluorescence observation of GFP downregulation 48 hours after GFP-22 siRNA transfection. The microscopic images on the right shows the downregulation of GFP compared to the control microscopic images on the left. siPORTT™ is a polyamine-based transfection agent used as a positive control. (A) No siRNA transfection; (B) siPORT™+GFP-22 siRNA; (C) PEG-EGCG+control siRNA; (D) PEG-EGCG+GFP-22 siRNA.

We found that 65.5% of the cells transfected with PEG-EGCG+control siRNA were in the high fluorescent region (FIG. 8 E). In cells transfected with PEG-EGCG+GFP-22 siRNA, the number of cells displaying a high fluorescence was reduced to 46.4% (FIG. 8 F). Therefore, when GFP-22 siRNA was delivered by PEG-EGCG, the reduction of GFP expression is about 19.1%. This shift in cells events from a region of high fluorescence intensity to low fluorescence intensity can be observed from the histogram.

Although the foregoing invention has been described in some detail by way of illustration and example, and with regard to one or more embodiments, for the purposes of clarity of understanding, it is readily apparent to those of ordinary skill in the art in light of the teachings of this invention that certain changes, variations and modifications may be made thereto without departing from the spirit or scope of the invention as described in the appended claims. Further, although individual embodiments are discussed the invention can include combinations of those embodiments.

We claim:

1. A conjugate comprising:
    (a) at least one polymer selected from the group consisting of amine-terminated poly(ethylene glycol) and succinimide-terminated poly(ethylene glycol), and
    (b) at least one flavonoid selected from the group consisting of amine-terminated (–)-epigallocatechin gallate, carboxyl-terminated (–)-epigallocatechin gallate, and succinimide-terminated (–)-epigallocatechin gallate (EGCG);
wherein the polymer is conjugated at the C6 and/or C8 of the A ring of the flavonoid; and wherein the flavonoid exists in a monomeric form or dimeric form before conjugation and remains in the monomeric form or dimeric form after conjugation.

2. The conjugate of claim 1, wherein the polymer comprises carboxyl-terminated poly(ethylene glycol), amine-terminated poly(ethylene glycol), or succinimide-terminated poly(ethylene glycol) and the flavonoid comprises (–)-epigallocatechin gallate (PEG-EGCG).

3. A delivery vehicle comprising a conjugate of claim 1.

4. An anti-cancer agent delivery vehicle comprising an anti-cancer agent and a conjugate of claim 1.

5. The anti-cancer agent delivery vehicle of claim 4, wherein the anti-cancer agent is a protein, a nucleic acid, a small molecule, a drug, a peptide, an antibody, a hormone, an enzyme, a growth factor, a cytokine, single stranded DNA, double stranded DNA, single stranded RNA, double stranded RNA, a short hairpin RNA, an siRNA, an antibiotic, a chemotherapeutic agent or an angiogenesis inhibitor.

6. The anti-cancer agent delivery vehicle of claim 5, wherein the anti-cancer agent is one selected from the group consisting of herceptin (trastuzumab), TNP470, doxorubicin, cisplatin, paclitaxel, daunorubicin, and a mixture thereof.

7. A pharmaceutical composition comprising the anti-cancer agent delivery vehicle of claim 4.

8. The pharmaceutical composition of claim 7, further comprising a pharmaceutically acceptable carrier.

9. The anti-cancer agent delivery vehicle according to claim 4 for use of delivering the anti-cancer agent to a cell in a subject.

10. The anti-cancer agent delivery vehicle of claim 9, wherein the anti-cancer agent delivery vehicle is formulated for injection, surgical implantation or topical administration.

11. The conjugate of claim 1, wherein the conjugate is of nanometer dimensions.

12. The conjugate of claim 1, comprising at least two flavonoids, wherein the flavonoids do not form oligomers with one another and wherein the flavonoids exists in a monomeric form or dimeric form before conjugation to the polymer and remain in the monomeric form or dimeric form after conjugation to the polymer.

* * * * *